United States Patent [19]

Eifler et al.

[11] 4,233,033
[45] Nov. 11, 1980

[54] METHOD AND APPARATUS FOR MEASURING THE O₂ CONTENT OF A GAS

[75] Inventors: Raymond J. Eifler, Farmington Hills; Walter F. Datwyler, Jr., Royal Oak,

[73] Assignee: Bendix Autolite Corporation, Fostoria, Ohio

[21] Appl. No.: 76,881

[22] Filed: Sep. 19, 1979

[51] Int. Cl.³ .............................................. G01N 27/4;
[52] U.S. Cl. .............................. 23/232 E; 73/27 R; 123/440; 324/65 R; 422/90; 422/98;
[58] Field of Search ................. 23/232 E; 422/90, 98; 123/119 R; 73/27 R; 204/195 S, 1 T; 324/71 SN, 71 R, 65 R;

[56] References Cited

U.S. PATENT DOCUMENTS

| | | | |
|---|---|---|---|
| 3,558,280 | 1/1971 | Pansonet al. | 422/90 |
| 3,915,135 | 10/1975 | Kushida et al. | 123/119 R |
| 4,147,513 | 4/1979 | Bienkowski et al. | 23/232 E |
| 4,151,503 | 4/1979 | Cermak et al. | 73/27 R |

OTHER PUBLICATIONS

Esper et al., "Titania Exhaust Gas Sensor for Automotive Applications", SAE/SP-79/441, 1979 Soc. of Auto. Eng., Inc.

*Primary Examiner*—R. E. Serwin
*Attorney, Agent, or Firm*—Raymond J. Eifler

[57] ABSTRACT

A method and apparatus for obtaining an electrical signal which is a function of the O₂ content of the exhaust gas of an internal combustion engine. Two resistors (1 and 3) are exposed to the exhaust gas of an internal combustion engine. Both resistors (1 and 3) have a resistance which varies as a function of the temperature of the exhaust gas to which it is exposed. However, the resistance of one of the resistors (1) also varies as a function of the oxygen content in the exhaust gas. Therefore, by applying a voltage to the resistors an electrical signal can be obtained which is a function of the O₂ content of the exhaust gas, with the temperature effect of the exahust gas on the network output being minimized or eliminated. The resistors (1 and 3) that form the sensing element (10) are connected in series with other resistors to form a first and second resistor network which is connected together in paralled circuit relationship.

21 Claims, 5 Drawing Figures

METHOD AND APPARATUS FOR MEASURING THE O₂ CONTENT OF A GAS

BACKGROUND OF THE INVENTION

This invention is related to an apparatus for sensing the $O_2$ content of an exhaust gas of an automobile engine. The invention is more particularly related to an improved resistance type oxygen sensor having a titania resistor and a zirconia resistor.

Internal combustion engines, particularly automotive internal combustion engines, have exhaust gases which contain carbon monoxide, nitrogen oxides, and non-oxidized hydrocarbons, i.e. unburned or only partially burned hydrocarbons. All these substances contribute to air pollution. In order to reduce these substances which cause air pollution to a minimum value, it is necessary to clean the exhaust gases from the internal combustion engines as much as possible by effectively removing the largest possible quantity of these substances from the exhaust gases. This means that carbon monoxide and unburned hydrocarbons should be oxidized as completely as possible into their next higher oxidation stage, namely carbon dioxide and water (for the hydrocarbons), and the nitrogen-oxide compound should be converted to elemental nitrogen and oxygen.

Conversion of the noxious components of exhaust gases to nonpoisonous compounds like carbon dioxide, nitrogen and water can be obtained by subjecting the exhaust gases to after-burning, i.e., subjecting them to temperatures above about 600° C. while exposing them to catalysts. In order to succeed in this method, however, the composition of the exhaust gases must be so controlled that practically complete conversion of the exhaust gases to the non-poisonous compounds is possible. This means that the relationship of air to fuel is close to the stoichiometric value. As a measure of the air to fuel mixture, the symbol lambda has been used. At a value of lambda equal to one, the relationship of air to fuel is stoichiometric. If no excess oxygen is present which exceeds the equilibrium of the various possible reactions, lambda is less than one. If, however, lambda is greater than one, excess oxygen is present in the mixture.

To ensure a value of lambda of approximately one over varying engine conditions requires that a sensing element be provided which is exposed to the exhaust gases and which determines oxygen content; this sensing element is then connected to a control device which controls the fuel or air supply and provides the correct ratio of fuel and air mixture to the internal combustion engine so that the exhaust gases will have as low a value of noxious components as possible.

Sensing elements which operate on the principle of elemental oxygen concentration and utilizing ion conductive solid electrolytes and electrodes have been used. The principles on which a solid electrolyte sensor operates is explained in great detail in U.S. Reissue Pat. No. Re 28,792, reissued Apr. 27, 1976 (previously U.S. Pat. No. 3,400,054). This patent illustrates a solid electrolyte oxygen sensor which, when one side is exposed to exhaust gases and on the other side exposed to ambient air, provides an electrical signal which is a function of elemental oxygen concentration; both sides of the solid electrolyte are covered at least in part with platinum to form electrodes. The electrolyte is generally stabilized zirconia. Another example of such a sensor may be found in U.S. Pat. No. 3,978,006 entitled "Methods for Producing Oxygen-Sensing Element, Particularly For Use With Internal Combustion Engine Exhaust Emission Analysis", issued Aug. 31, 1976.

Another type of oxygen sensor is one wherein the electrical resistance of the sensor changes with the amount of oxygen present in the gas. This type of sensor is generally referred to as a resistance type sensor and the principle of operation of such a sensor is explained in U.S. Pat. No. 3,558,280 entitled "Solid-State Oxygen Gage" issued Jan. 22, 1971. The use of a titania resistor sensor in a wheatstone bridge circuit to obtain a signal to control the air-fuel ratio of an internal combustion engine as explained in U.S. Pat. No. 3,915,135 entitled "Circuit for Converting a Temperature Dependent Input Signal to a Temperature Independent Output Signal" issued Oct. 28, 1975.

The resistance type (titania) oxygen sensor has certain disadvantages. For instance, the titania sensor must operate over a range from 300° C. to 900° C., but the electrical resistance of the sensor, over the entire range, does not change in a manner that permits a delineation between a lean air-fuel mixture and a rich air-fuel mixture. Specifically, for a lean air-fuel mixture over the range of 300° C. and 900° C., the dc resistance of a titania sensor drops from $3 \times 10^{10}$ ohms down to about $2 \times 10^{\alpha}$ ohms. While the dc resistance for a rich air-fuel mixture, over the same range, varies from $5 \times 10^4$ ohms down to about 70 ohms. Therefore, at certain temperatures, the resistance characteristics for a rich and a lean mixture for the sensor overlap and it is impossible, with an uncompensated titania sensor, to determine whether the air-fuel ratio is rich or lean. Of course, this is undesirable, as it would not be possible to control the air-fuel mixture because the titania type sensor cannot distinguish between a rich air to fuel mixture and a lean air to fuel mixture.

An example of a gas sensor of titania ceramic material which includes a circuit for converting a temperature dependent input signal to a temperature independent output signal to control the air to fuel ratio of an automobile engine is shown in previously mentioned U.S. Pat. No. 3,915,135.

Another example of an $O_2$ sensor system that provides an electrical signal indicative of the $O_2$ content of an exhaust gas which minimizes the temperature effect on the signal is U.S. Pat. No. 4,147,513 entitled "Method and Apparatus for Measuring the $O_2$ Content of a Gas" issued Apr. 3, 1979. This $O_2$ sensor system and apparatus describes the use of titania and zirconia resistors connected together in series to obtain a signal which is indicative of the $O_2$ content in the gas.

SUMMARY OF THE INVENTION

This invention provides an oxygen sensing system which essentially nullifies the effect of temperature of the gas on an oxygen sensing element and is an alternate approach to the system shown in previously discussed U.S. Pat. Nos. 4,147,513 and 3,915,135.

The invention is a method and apparatus for sensing the $O_2$ content of a gas and is characterized by an electrical circuit that includes a titania resistor (1) that is in parallel circuit relationship with a zirconia resistor (3). When voltage is applied to the circuit and the resistors are exposed to a heated gas, an electrical signal can be generated from the circuit that is a function of the oxygen content of the gas.

Accordingly, it is an object of this invention to provide a method and apparatus for determining the relative $O_2$ content of a gas.

It is another object of this invention to provide an oxygen sensing apparatus and method which performs well at temperatures from below 350° C. to above 850° C.

It is another object of this invention to provide a simply constructed oxygen sensing system using inexpensive electronic circuitry.

It is still another object of this invention to provide an oxygen sensing system which will not require adjustment of the electronic circuitry upon an installation or upon replacement of the sensor.

It is another object of this invention to improve the performance of an oxygen sensing system and method using a titania type oxygen sensor by minimizing the effect of temperature on said sensor.

The above and other features and objects of this invention will become apparent from the following detailed description taken in conjunction with the accompanying drawings and claims which form a part of this specification.

DETAILED DESCRIPTION OF THE DRAWINGS

Figure 1:
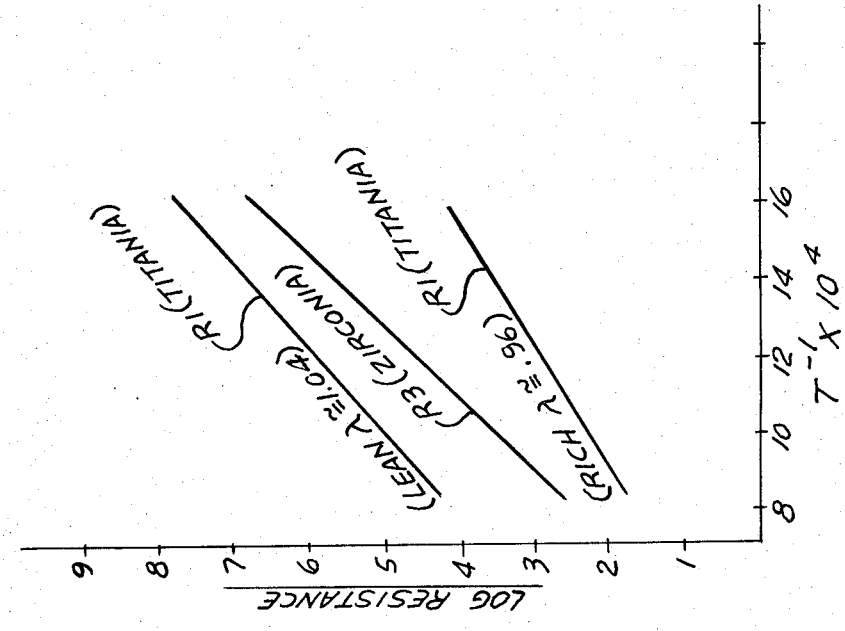
FIG. 1 is a graph of the resistance of a titania resistor and a zirconia resistor versus temperature when exposed to the exhaust gas of an engine.

FIG. 1 is a graph which illustrates the resistance versus temperature of a titania resistor and a zirconia resistor when the resistors are exposed to the exhaust gas of an internal combustion engine. The y axis is the resistance of each of the resistors on a log scale to the base 10. The x axis is calculated from the formula of $1/T \times 10^4$ where T is temperature in °K. The curves marked R1 rich and R1 lean indicate the resistance values of the titania resistor over a range of operating temperature for lambda equal to 0.96 and 1.04 respectively. R3 illustrates the resistance values over the same temperature range for a zirconia resistor. The resistance of the zirconia resistor being substantially the same regardless of the air to fuel ratio, i.e. changes in lambda. This graph illustrates that when the resistance of the titania resistor is greater than the resistance of the zirconia resistor, there is a lean air to fuel mixture. Conversely, when the value of the titania resistor is less than the resistance of the zirconia resistor, there is a rich air to fuel mixture.

Figure 2:
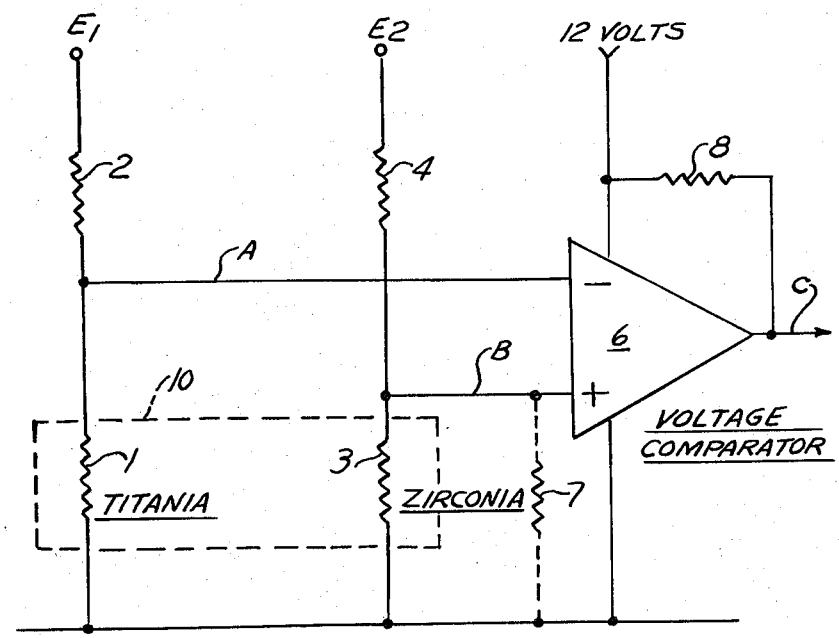
FIG. 2 is a schematic diagram of the electrical circuit used to accomplish the principles of this invention.

FIG. 2 illustrates an electrical circuit that accomplishes the principles of this invention. The circuit consists of a first resistor network comprised of a titania resistor 1 in series with a second resistor 2, a second resistor network comprised of a zirconia resistor 3 and a fourth resistor 4. A comparator 6 receives signals A and B which are an indication of the voltages across the titania resistor and the zirconia resistors respectively. A voltage is applied to the resistor networks at E1 and E2 by an appropriate dc voltage source. The titania resistor 1 and zirconia resistor 3 comprise the sensing element 10 which is exposed to the exhaust gas of an internal combustion engine.

The resistance of the titania resistor 1 varies as a function of both the temperature and the oxygen content of the exhaust gas from the engine. The resistance of the zirconia resistor 3 varies only as a function of the temperature of the exhaust gas. The resistor 3 is chosen so that its temperature characteristic is substantially the same as the temperature characteristic of the titania resistor 1. The zirconia resistor may be replaced by any other resistor that exhibits a change in resistance with respect to temperature that is similar to the titania resistor or changes proportionately about the same. For instance, it has been suggested in a Society of Automotive Engineers 1979 article entitled "Titania Exhaust Gas Sensor For Automotive Applications" that the two resistors be comprised of titania. In this article, it is suggested that one of the oxygen sensing elements be comprised of a porous $TiO_2$ ceramic and the other resistor may be comprised of a densified $TiO_2$ ceramic which would be utilized as a matching thermistor for temperature compensation. This is because densified titania ceramic is relatively insensitive to oxygen changes. Treating the titania resistor 1 with a precious metal such as platinum may also be used to improve its low temperature response.

EXAMPLES

The following is a table identifying the values of components used in operable embodiments of the invention:

| Element No. | Example I | Example II | Example III |
| --- | --- | --- | --- |
| 1 | Titania Resistor | Same | Same |
| 2 | $9 \times 10^5$ ohms | 71.6K ohms | 71.6K ohms |
| 3 | Zirconia Resistor | Same | Same |
| 4 | $2 \times 10^4$ ohms or $2 \times 10^5$ ohms | 71.6K ohms | 71.6K ohms |
| E1 | 10 volts | | Same |
| E2 | 5 volts | | 10 volts |
| 6 | comparator National Semiconductor LM-239 | Same | Same |
| 7 | None | None | 644 K ohms |
| 8 | 5K ohms | 5K ohms | 5K ohms |

Typical examples of the resistance of resistors 1 and 3 at different temperatures are as follows:

For a rich air to fuel mixture, the resistance of the zirconia resistor 3 at 400° C. is $1.6 \times 10^6$ ohms and 750° C., 2.6 K ohms; for the same air to fuel mixture and temperature range the resistance of the titania resistor 1 is 7.6 K ohms and 180 ohms respectively; for a lean air-fuel mixture, the resistance of the zirconia resistor at 400° C. is $1.6 \times 10^6$ ohms and at 750° C., 2.6 K ohms; and for the same air to fuel mixture and temperature range, the resistance of the titania resistor is about $2 \times 10^7$ ohms and 89 K ohms respectively.

Figure 3:
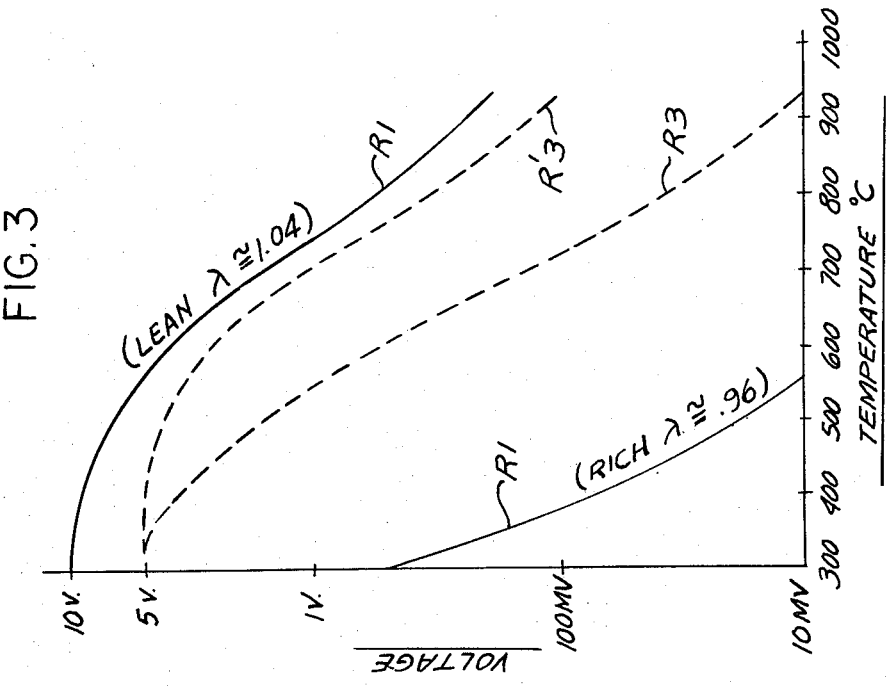
FIG. 3 is a graph of voltages versus temperature for the circuit shown in FIG. 1 and described in Example I.

FIG. 3 is a graph of voltage versus temperature for the circuit shown in FIG. 1 and described in Example I. The y coordinate is voltage on a log scale and the x coordinate is temperature in degrees centigrade. Curve R1 (rich) indicates the values of voltage across the titania resistor as a function of temperature when lambda equals approximately 0.96 and the Curve R1 (lean) indicates the voltage across the titania resistor versus temperature when lambda equals 1.04. The remaining two curves R3 and R'3 indicate the voltage-temperature characteristics of the zirconia resistor for two different values of the series resistor 4. R3 illustrates the temperature and voltage characteristics of the zirconia resistor when resistor 4 is about $2 \times 10^5$ ohms. Similarly, Curve R'3 indicates the voltage and temperature characteristics of the zirconia resistor when resistor 4 is $2 \times 10^4$ ohms. This graph illustrates that by careful selection of the resistor 4 connected in series with the zirconia resistor 3 the difference in voltages between the voltage across the titania resistor 1 and the zirconia resistor 3 can be made larger to facilitate operation of the comparator 6 shown in FIG. 2.

Figure 4:
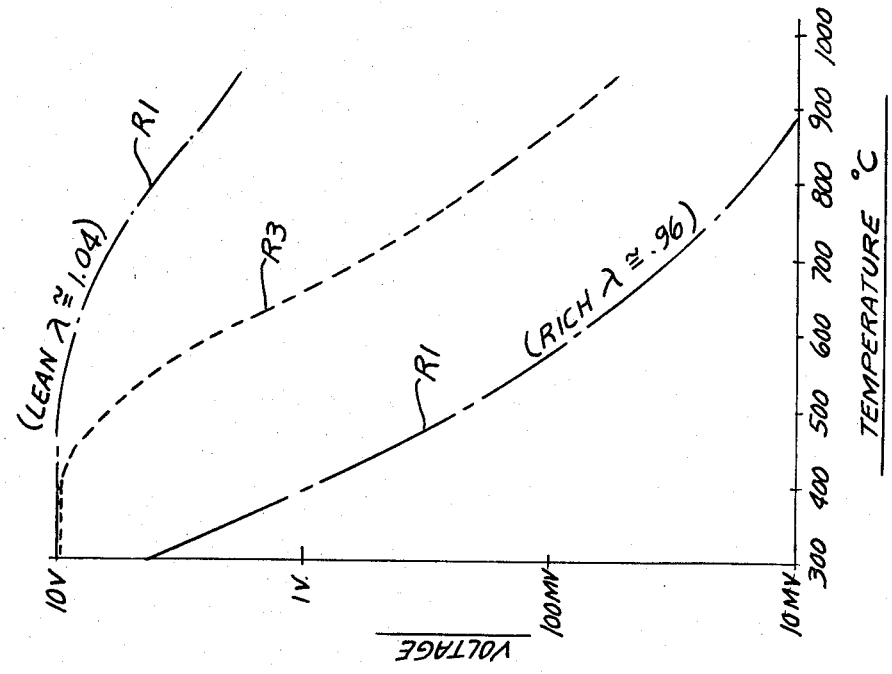
FIG. 4 is a graph of voltages versus temperature for the circuit shown in FIG. 1 and described in Example II.

FIG. 4 is a similar graph of voltage versus temperature for the circuit shown in FIG. 1 and described in Example II. In this embodiment the values of resistors 2 and 4 are equal and the total voltage is applied across both resistors 3 and 4. Curve R1 (rich) and R1 (lean) indicates the voltage-temperature characteristics of the titania resistor 1 when the air-fuel ratio (lambda) is equal to 0.96 and 1.04 respectively. R3 illustrates the voltage-temperature characteristics of the zirconia resistor. For the network conditions of Example II the voltages into the comparator, i.e. $R_1$ (lean) and $R_3$, approach the $E1 = E2 = 10VDC$ value at low temperatures, but are still sufficiently different for operation of the comparator at 300° C. nominal.

Figure 5:
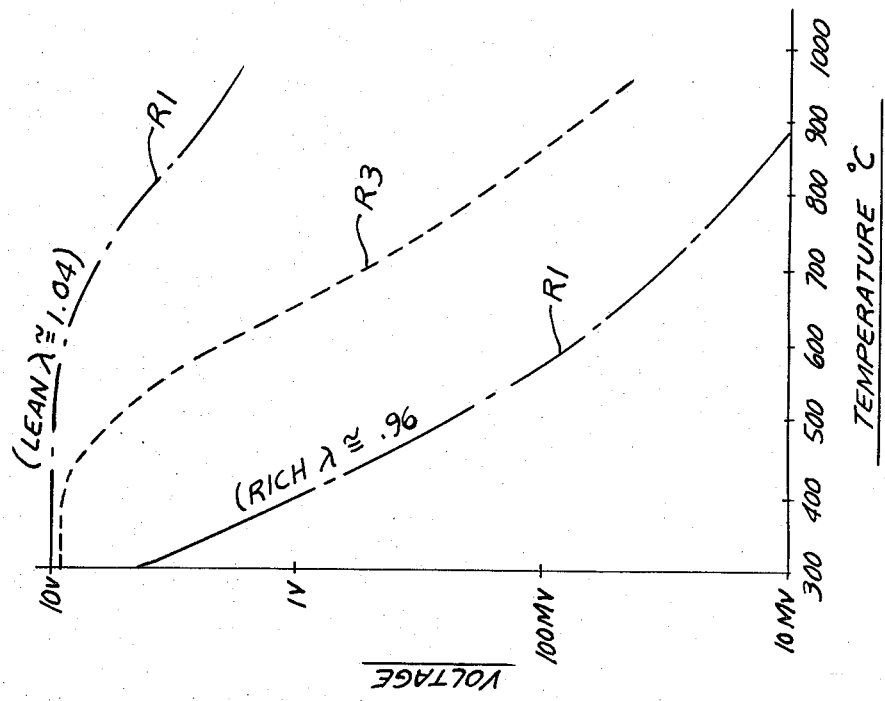
FIG. 5 is a graph of voltages versus temperature for the circuit shown in FIG. 1 and described in Example III.

FIG. 5 is a similar graph of voltage versus temperature for the circuit shown in FIG. 1 and described in Example III. In this embodiment of the invention a resistor 7 was added to the circuit shown in FIG. 2 to increase the difference in the voltages across the zirconia resistor and the titania resistor when the air-fuel ratio was lean and the temperature was less than 500° Centigrade.

OPERATION

In operation, the comparator 6 compares the voltage signal A from across the titania resistor 1 to the voltage signal B from across the zirconia resistor 3 and provides output signals when the signal A is greater and less than signal B.

Since the voltage across the titania resistor 1 is a function of the oxygen content in a gas to which it is exposed, signal A is a function of the $O_2$ content in the exhaust gas.

When voltage is applied to the circuit at points E1 and E2 and resistors 1 and 3 are inserted in the exhaust gas from an internal combustion engine, the output signals A and B from the circuit will provide an indication of the temperature and oxygen content of the exhaust gas and therefore can be useful in determining and adjusting the air to fuel ratio entering such engine.

When the resistors 1 and 3 are exposed to an exhaust gas, the temperature of the exhaust gas will change the resistance of both resistors 1 and 3. However, since both resistors have been chosen to have resistances which vary about the same percentage with temperature, the voltage across both resistors 1 and 3 should change about the same amount. However, when the oxygen content of the exhaust gas decreases, the resistance of the titania resistor 1 will decrease and when the oxygen content of the exhaust gas increases, the resistance of the titania resistor 1 will increase. This means that when there is a rich air to fuel mixture going into the engine, the $O_2$ content in the exhaust gas is less than it would be when the exhaust gas is a result of a lean air to fuel mixture. Conversely, when the titania resistor 1 is exposed to an exhaust gas having more oxygen, i.e. a lean air to fuel mixture, the voltage across the titania resistor increases while the voltage across the zirconia resistor 3 does not. The signals A and B from the titania and zirconia resistors are fed into the input of a comparator 6 which compares the signals A and B together and provides one output signal C when A is greater than B and another output signal when A is less than B.

While preferred embodiments of this invention have been disclosed, it will be apparent to those skilled in the art that changes may be made to the invention as set forth in the appended claims and, in some cases, certain features of the invention may be used to advantage without corresponding use of other features. For example, while only titania and zirconia have been shown in the graphs it has been suggested that other material may be used for the zirconia resistor so long as the resistance vs temperature characteristics of both resistors exposed to the exhaust gas are substantially similar or change in equal proportions, and so long as one of the materials has a resistance which varies substantially more than the other resistor with the $O_2$ content of the exhaust gas to which it is exposed. Accordingly, it is intended that the illustrative and descriptive material herein be used to illustrate the principles of the invention and not to limit the scope thereof.

Having described the invention, what is claimed is:

1. A method for obtaining an electrical signal which is a function of the oxygen content in an exhaust gas of an internal combustion engine, the method comprising:
    connecting a first resistor comprised of titania in series with a second resistor having a predetermined resistance;
    connecting a third resistor comprised of stabilized zirconia in series with a fourth resistor having a predetermined resistance;
    connecting the first and second resistors in parallel relationship with the third and fourth resistors;
    applying a potential across the resistors;
    exposing said resistors to the exhaust gas an internal combustion engine;
    obtaining a first electrical signal which is a function of the first and second resistors; and
    obtaining a second electrical signal which is a function of said third and fourth resistors.

2. The method as recited in claim 1 including the steps of comparing the first and second electrical signals and generating an output signal which is a function of said first and second signals.

3. The method as recited in claim 2 wherein the zirconia resistor has about the same resistance-temperature characteristics as said titania resistor over a predetermined temperature range of said gas.

4. The method as recited in claim 1, 2, or 3 wherein the voltage applied to said first and second resistors is larger than the voltage applied to said third and fourth resistors.

5. The method as recited in claim 1, 2 or 3 wherein the second and fourth resistors have the same values of resistance and wherein the voltage applied to said first and second resistors is larger than the voltage applied to said third and fourth resistors.

6. A method for obtaining an electrical signal which is a function of the $O_2$ content of a gas, the method comprising:

connecting a first resistor made of titania in series with a second resistor having a predetermined resistance, the resistance of the titania resistor varying as a function of both the temperature and the oxygen content of the gas to which it is exposed;

connecting a third resistor, the resistance of which varies as a function of the temperature of the gas to which it is exposed, to a fourth resistor having a predetermined resistance, said third resistor having about the same resistance-temperature characteristics as said titania resistor over a predetermined temperature range of said gas;

connecting said first and second resistor in parallel relationship with said third and fourth resistors;

applying a voltage across said resistors;

exposing said resistors to a gas;

obtaining a first electrical signal which is a function of the voltage across one of said first and second resistors;

obtaining a second electrical signal which is a function of the voltage across one of said third and fourth resistors; and generating an output signal from said first and second electrical signals which is a function of said first and second electrical signals.

7. The method as recited in claim 6 wherein the step of generating an output signal is accomplished by comparing said first electrical signal to said second electrical signal.

8. The method as recited in claim 7 wherein the first electrical signal is a function of the voltage across the first resistor.

9. The method as recited in claim 8 wherein the second electrical signal is a function of the voltage across the third resistor.

10. The method as recited in claim 6, 7, 8 or 9 wherein the voltage applied to said first and second resistors is larger than the voltage applied to said third and fourth resistors.

11. The method as recited in claim 6, 7, 8 or 9 wherein the resistance of the second and fourth resistors have the same values and wherein the voltage applied to said first and second resistors is larger than the voltage applied to said third and fourth resistors.

12. An electrochemical oxygen sensing apparatus for obtaining an electrical signal which is a function of the oxygen content in a gas, said sensing apparatus comprising:

a first resistor having a resistance which varies as a function of the temperature and oxygen content of the gas to which it is exposed;

a second resistor having a resistance r1;

a third resistor having a resistance which varies as a function of the temperature of the gas to which it is exposed;

a fourth resistor having a resistance r2;

means for electrically connecting said first resistor in series with said second resistor;

means for electrically connecting said third resistor in series with said fourth resistor;

means for electrically connecting said first and second resistor in parallel relationship with said third and fourth resistor; and means for applying voltage across said first and second resistor and said third and fourth resistor; and means for generating an output signal which is a function of the voltage across the first resistor and the voltage across said third resistor, whereby when a voltage is applied to said resistors and said first and third resistors are exposed to a gas, said output signal is related to the oxygen content of the gas.

13. The apparatus as recited in claim 12 wherein the means for generating an output signal includes a comparator for comparing a first signal which is a function of the voltage across said first resistor to a second signal which is a function of the voltage across said third resistor.

14. The apparatus as recited in claim 12 or 13 wherein said third resistor is comprised of zirconia.

15. The apparatus as recited in claim 12 or 13 wherein said first resistor is comprised of titania.

16. The method as recited in claim 12 or 13 wherein the voltage applied to said first and second resistors is larger than the voltage applied to said third and fourth resistors.

17. The method as recited in claim 12 or 13 wherein the resistors r1 and r2 have the same values and wherein the voltage applied to said first and second resistors is larger than the voltage applied to said third and fourth resistors.

18. An electrochemical oxygen sensing apparatus for obtaining an electrical signal which is a function of the oxygen content in a gas, said sensing apparatus comprising:

a first resistor comprised of a titania material;

a second resistor having a resistance r1;

a third resistor comprised of a material, the resistance of which varies as a function of the temperature of the gas to which it is exposed, said third resistor having about the same resistance-temperature characteristics as said first resistor over a predetermined temperature range of said gas;

a fourth resistor having a resistance r2;

means for electrically connecting said first resistor in series with said second resistor;

means for electrically connecting said third resistor in series with said fourth resistor;

means for electrically connecting said first and second resistor network in parallel with said third and fourth resistor network;

means for applying a voltage across said first and second resistor and said third and fourth resistor;

means for obtaining a first electrical signal which is a function of the voltage across said first resistor;

means for obtaining a second electrical signal which is a function of the voltage across said third resistor; and means for comparing said first electrical signal to said second electrical signal and providing an output signal.

19. The apparatus as recited in claim 18 wherein said third resistor is comprised of zirconia.

20. The method as recited in claim 18 or 19 wherein the voltage applied to said first and second resistors is larger than the voltage applied to said third and fourth resistors.

21. The method as recited in claim 18 or 19 wherein the resistors r1 and r2 have the same values and wherein the voltage applied to said first and second resistors is larger than the voltage applied to said third and fourth resistors.

* * * * *